US012558318B2

(12) United States Patent
Chystyakov-Malinovski et al.

(10) Patent No.: US 12,558,318 B2
(45) Date of Patent: Feb. 24, 2026

(54) POWDERED PLANT PREPARATION, THE MANNER IN WHICH IT IS OBTAINED, MICROGRANULES AND TABLETS OBTAINED FROM THAT PREPARATION AND THE WAYS OF PRODUCING THEM

(71) Applicant: BIOFITON SP. ZO.O., Warsaw (PL)

(72) Inventors: Oleksiy Chystyakov-Malinovski, Charkow (UA); Jozef Smoczynski, Warsaw (PL)

(73) Assignee: BIOFITON SP. ZO.O., Warsaw (PL)

( * ) Notice: Subject to any disclaimer, the term of this patent is extended or adjusted under 35 U.S.C. 154(b) by 1037 days.

(21) Appl. No.: 17/630,281

(22) PCT Filed: Jul. 27, 2020

(86) PCT No.: PCT/PL2020/050053
§ 371 (c)(1),
(2) Date: Jan. 26, 2022

(87) PCT Pub. No.: WO2021/020978
PCT Pub. Date: Feb. 4, 2021

(65) Prior Publication Data
US 2022/0273577 A1      Sep. 1, 2022

(30) Foreign Application Priority Data

Jul. 27, 2019      (PL) ........................................ 430717

(51) Int. Cl.

| | |
|---|---|
| A61K 9/19 | (2006.01) |
| A61K 9/16 | (2006.01) |
| A61K 9/20 | (2006.01) |
| A61K 36/11 | (2006.01) |
| A61K 36/15 | (2006.01) |
| A61K 36/185 | (2006.01) |
| A61K 36/23 | (2006.01) |
| A61K 36/236 | (2006.01) |
| A61K 36/24 | (2006.01) |
| A61K 36/28 | (2006.01) |
| A61K 36/288 | (2006.01) |
| A61K 36/35 | (2006.01) |
| A61K 36/45 | (2006.01) |
| A61K 36/48 | (2006.01) |
| A61K 36/533 | (2006.01) |
| A61K 36/534 | (2006.01) |
| A61K 36/54 | (2006.01) |
| A61K 36/68 | (2006.01) |
| A61K 36/70 | (2006.01) |
| A61K 36/704 | (2006.01) |
| A61K 36/72 | (2006.01) |
| A61K 36/73 | (2006.01) |
| A61K 36/734 | (2006.01) |
| A61K 36/738 | (2006.01) |
| A61K 36/76 | (2006.01) |
| A61K 36/77 | (2006.01) |
| A61K 36/899 | (2006.01) |
| A61K 36/9068 | (2006.01) |

(52) U.S. Cl.
CPC .............. *A61K 9/19* (2013.01); *A61K 9/1623* (2013.01); *A61K 9/1652* (2013.01); *A61K 9/1694* (2013.01); *A61K 9/2095* (2013.01); *A61K 36/11* (2013.01); *A61K 36/15* (2013.01); *A61K 36/185* (2013.01); *A61K 36/23* (2013.01); *A61K 36/236* (2013.01); *A61K 36/24* (2013.01); *A61K 36/28* (2013.01); *A61K 36/288* (2013.01); *A61K 36/35* (2013.01); *A61K 36/45* (2013.01); *A61K 36/48* (2013.01); *A61K 36/533* (2013.01); *A61K 36/534* (2013.01); *A61K 36/54* (2013.01); *A61K 36/577* (2024.05); *A61K 36/68* (2013.01); *A61K 36/70* (2013.01); *A61K 36/704* (2013.01); *A61K 36/72* (2013.01); *A61K 36/73* (2013.01); *A61K 36/734* (2013.01); *A61K 36/738* (2013.01); *A61K 36/76* (2013.01); *A61K 36/77* (2013.01); *A61K 36/899* (2013.01); *A61K 36/9068* (2013.01); *A61K 2236/15* (2013.01); *A61K 2236/51* (2013.01)

(58) Field of Classification Search
CPC ....................................................... A61K 9/19
See application file for complete search history.

(56) References Cited

U.S. PATENT DOCUMENTS

| | | | |
|---|---|---|---|
| 3,838,825 | A | 10/1974 | Haas et al. |
| 5,513,809 | A | 5/1996 | Perkel |

FOREIGN PATENT DOCUMENTS

| | | | | |
|---|---|---|---|---|
| CN | 109174407 | A | | 1/2019 |
| JP | S58210023 | A | | 12/1983 |
| KR | 20030087024 | A | * | 11/2003 |
| KR | 2010005165 | A | * | 1/2010 |
| PL | 412851 | A1 | | 1/2017 |

OTHER PUBLICATIONS

International Search Report and Written Opinion issued in corresponding International Patent Application No. PCT/PL2020/050053 dated Dec. 16, 2020 (14 pages).
Tanja Hanke, "Kryogene Probenvorbereitung," Sonderthema: Probenvorbereitung, vol. 112, No. 6, Jun. 1, 2016, pp. 238-242 (See PCT Search Report for relevance).

* cited by examiner

*Primary Examiner* — Qiuwen Mi
(74) *Attorney, Agent, or Firm* — Kilyk & Bowersox, P.L.L.C.

(57) ABSTRACT

Disclosed is a powdered plant preparation and a method for its preparation, as well as microgranules and tablets obtained therefrom, and methods for their preparation. The invention is suitable for use in the production of herbal preparations.

21 Claims, 3 Drawing Sheets

POWDERED PLANT PREPARATION, THE MANNER IN WHICH IT IS OBTAINED, MICROGRANULES AND TABLETS OBTAINED FROM THAT PREPARATION AND THE WAYS OF PRODUCING THEM

This application is a National Stage Application of PCT/PL2020/050053, filed Jul. 27, 2020, which claims priority to Polish Patent Application No. P.430717, filed Jul. 27, 2019.

The invention concerns a powdered plant preparation and the way it is obtained, as well as the microgranules and tablets obtained from this preparation and the way they are produced.

The invention is suitable for use in the production of herbal preparations.

Current Technical Situation

Various forms of plant preparations are known for health-promoting and medicinal applications. These preparations, in their simplest form, take the form of herbal mixtures for making infusions, decoctions and macerates. The more perfect form are granules, tablets and capsules made from powdered or extruded plant materials and their mixtures. In the case of medicinal preparations, the aim is to isolate a group of substances from the active raw material. Such preparations are used in the form of extracts for making granulates, tablets, capsules, pastes and liquid forms of medicines.

There are many types of vibrating mills suitable for grinding various materials, especially under cryogenic conditions.

For example, the U.S. Pat. No. 3,838,825 patent description reveals a vibrating mill with a horizontal vibrating grinding chamber covered with thermal insulation material, which allows the material to be milled using the vibrating method at a selected temperature, especially with simultaneous cooling.

The U.S. Pat. No. 5,513,809 patent description reveals a vibrating mill for grinding in cryogenic conditions of various types of raw materials, especially minerals, plastics, spices or cosmetics. Despite the availability of various forms of plant preparations and methods of producing them, there is still a need for improved forms and easy to implement ways of producing them.

Aim of the Invention

The aim of the invention is to develop a product obtained directly from plant material with new improved properties. The desired form of a plant preparation should be more effective than traditional herbal preparations, and in particular it should have a higher content of biologically active substances and high bioavailability compared to the plant material. It is particularly desirable for the obtained plant prepared to have a higher content of active extractable soluble substances in water than the herbal mixtures used in its manufacture, which have been ground using traditional techniques. At the same time, the obtained plant preparation should be stable and free of any preservatives.

In connection with the production of such a preparation, the aim of the invention is to provide an effective way of milling plant material. Plant material is a raw material that is difficult to grind. The problem results from the size and elasticity of plant cells, inside which most of the desired active substances are contained. The size of plant cells ranges from 30 μm to 60 μm (average size 50 μm) and they usually have some plasticity.

It is desirable that the resulting plant preparation is in a solid form and suitable for further processing into the final form of oral plant preparations such as granules for encapsulation or tabletting. In the case of obtaining a solid preparation in the form of a powder, further processing of such a raw material in the production of the preparation's final form is a serious problem. A known technique for preventing these problems is granulation, which consists in processing powdered medicinal substances and excipients into homogeneous grains (aggregates). The granulated product can be a ready-made form of medicine or an intermediate product for tablet making. The problem with the production of granules is the choice of a more suitable excipient, which, when used in a minimum quantity, ensures easy granulation without reducing the active substance content of the obtained granules.

The Essence of the Invention

The inherent problems described above were solved in this invention.

The subject of the invention are the methods and products defined in the claims.

DETAILED DESCRIPTION OF THE INVENTION

Figure 1A:
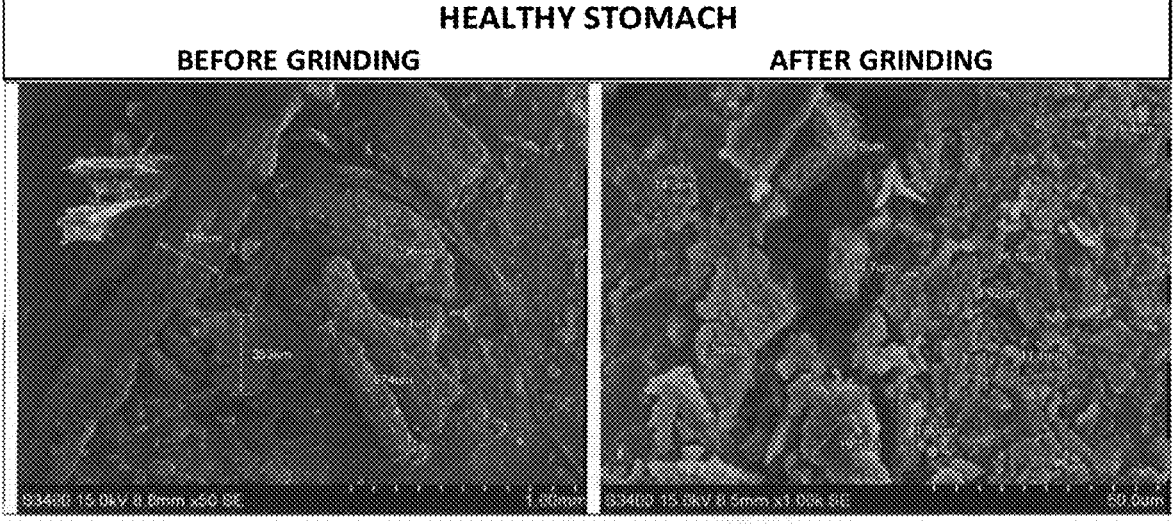
FIG. 1A shows microscope photos with determined particle sizes of "healthy stomach" and "healthy pancreas" before and after grinding.
Figure 1A:
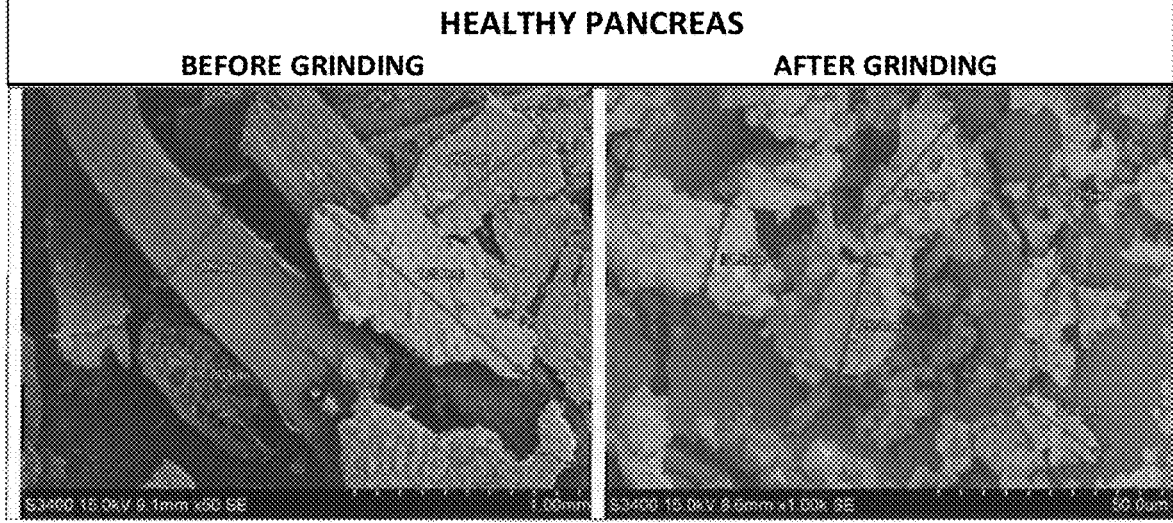

The method of vibratory cryogenic grinding developed in accordance with the invention allowed to solve the problems described above. The method according to the invention is free from defects of traditional methods of extraction of biologically active substances from plant material. When processing plant material according to the invention, the active substances are not subjected to radical process conditions (such as action of reagents, elevated temperature, etc.) and therefore they are preserved in natural forms and proportions. Therefore, the method according to the invention allows to keep the maximum amount of biologically active substances and prevents their degradation.

Unexpectedly, a plant preparation according to the invention is characterized by a higher content of water-soluble active extractive substances than the herbal mixtures used in its production, which are ground by traditional techniques.

According to the invention method, in order to ensure the release of active substances contained in plant cells, the plant material is ground to a size of not more than 30 μm, i.e. less than the size of the cells. This ensures that the vast majority of active substances in the cells are released. According to the results of the research carried out, during the implementation of the method according to the invention, the concentration in the preparation of easily accessible natural biological active substances, in particular vitamins, increases almost tenfold due to their release from interactions with other components and structures of plant cells and the transition from a bound to a free state. At the same time, the vitamins contained in the plant preparation obtained in accordance with the invention have the form of natural chelate compounds, which are assimilated by the organism.

The preparation is obtained in the form of powder, which is suitable for direct application or may be further processed, e.g. granulated.

Subsequently obtained granulate gained from the powdered plant preparation contains a minimum amount of excipients selected in accordance with the invention, which when used in a minimum amount ensure easy granulation without lowering the content of soluble active substances in the obtained granulate.

In order to better explain the essence of the invention, its description has been illustrated by the following implementation components, which should not, however, be equated with the full scope of the invention.

Example 1: Method of Obtaining a Powdered Plant Preparation

In order to obtain a powdered plant preparation, the initial plant material, which can be any mixture of plant material, is subjected to cryogenic vibration milling with any commercially available vibratory mill capable of milling under cryogenic conditions and the operating temperatures and vibration frequencies used in the method. An example of a suitable device for this purpose can be an appropriately equipped vibrating mill offered by MBE Coal & Minerals Technology GmbH, especially such as the CRYOPALLA model for liquid nitrogen cooling or a similar device suitable for operating temperatures and vibration frequencies. It is desirable that the ground herbs have a water content of 6 to 8% by weight. Most often in order to obtain such water content it is necessary to pre-dry the herbs.

Especially when using a mix of different herbs, it is also beneficial to pre-clean, grind (e.g. in a temperature controlled mechanical mill) and mix them in a herbal mixer for 15 to 20 minutes. The pre-treatment of herbs should be carried out under conditions which prevent degradation of the active substances of such herbs, in particular it should not be carried out at too high a temperature.

The plant material is placed in the cooled mill chamber. The cooling system is then activated and the plant material is frozen. Pre-cooling is carried out for about 1 hour by introducing liquid nitrogen into the cooling system under a pressure of 0.15 to 0.25 atm. The temperature of the coolant being introduced is from −185° C. to −110° C., preferably about −130° C. on average, and the gas temperature leaving the cooling system is from −40° C. to −15° C., preferably about −30° C. on average. It is advantageous to freeze the plant material to a temperature below −90° C., preferably to a temperature between −150° C. and −110° C.

Before milling, the liquid nitrogen supply to the cooling system is closed for about 3-5 minutes and then the milling process commences by starting the mill's electric drive from the control panel and setting the vibration frequency above 30 Hz, preferably in the range from 35 to 37 Hz. After obtaining the appropriate frequency of operation of the vibrating mill, the supply of the coolant to the cooling system is reopened by controlling the cooling conditions as described above, and the grinding process is carried out by grinding the frozen plant material for 1 minute to 15 minutes, preferably for 5 to 10 minutes. The grinding is carried out at a temperature ranging from −150° C. to −15° C., with favourable grinding below −70° C., particularly favourable below −90° C.

Keeping the above-mentioned temperature conditions and milling time, the milling of frozen material can be performed in a continuous mode by gradually adding the frozen material to the milling chamber and receiving the milled product at the same time. It is also possible to use a vibrating mill with more than one grinding chamber, which are arranged sequentially in the process sequence. In such a situation, it may be necessary to freeze the material to a temperature below −90° C., preferably to a temperature between −150° C. and −110° C., before placing it in the next grinding chamber. Cooling of the plant material before the first or subsequent vibrating milling can also be carried out by contacting it with the liquid nitrogen stream immediately before or during pouring into the milling chamber.

In order to normalise the grain size of the powder obtained and, above all, to separate plant fragments which have not been milled properly, it is beneficial to sieve the powder obtained through a sieve with a mesh size ranging from 400 μm to 150 μm. For properly prepared plant material and properly performed grinding, the amount of residue not passing through the sieve should not exceed 10%.

It is advantageous to heat the powdered preparation to room temperature before further processing. For this purpose, the screened powder can be placed in aluminium containers (barrels) and stored at room temperature for approximately 17 hours.

Example 2: Characteristics of a Plant Preparation in Powder Form

The powdered plant preparation obtained by the method according to the invention was subjected to detailed analysis. The size of the grains forming the powder and the content of water-soluble extracts were examined.

Particle Size

Figure 1B:
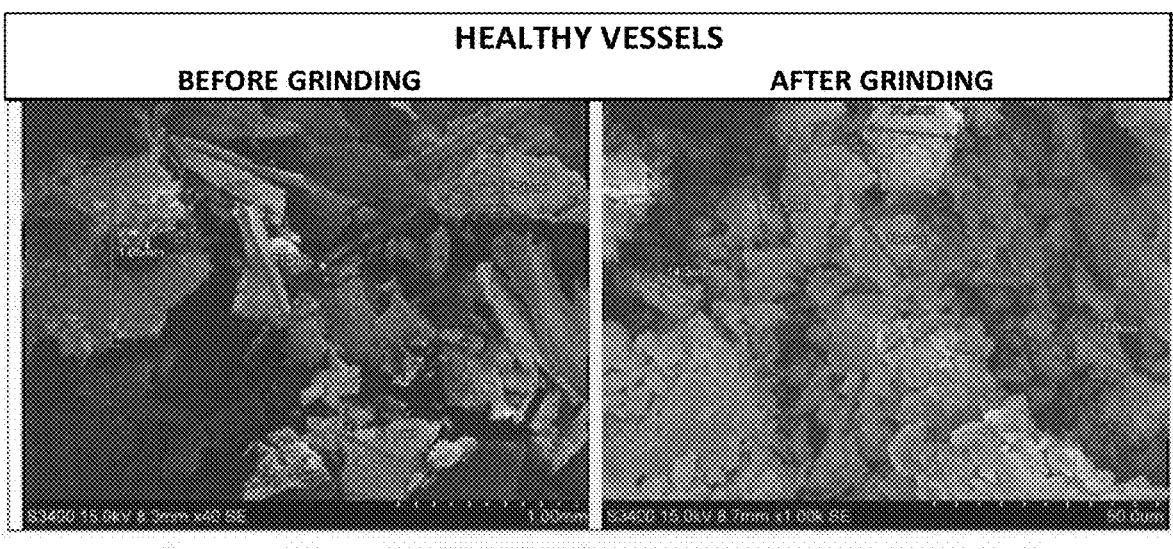
FIG. 1B shows microscope photos with determined particle sizes of "healthy vessels", "healthy joints", and "healthy kidneys" before and after grinding.
Figure 1B:
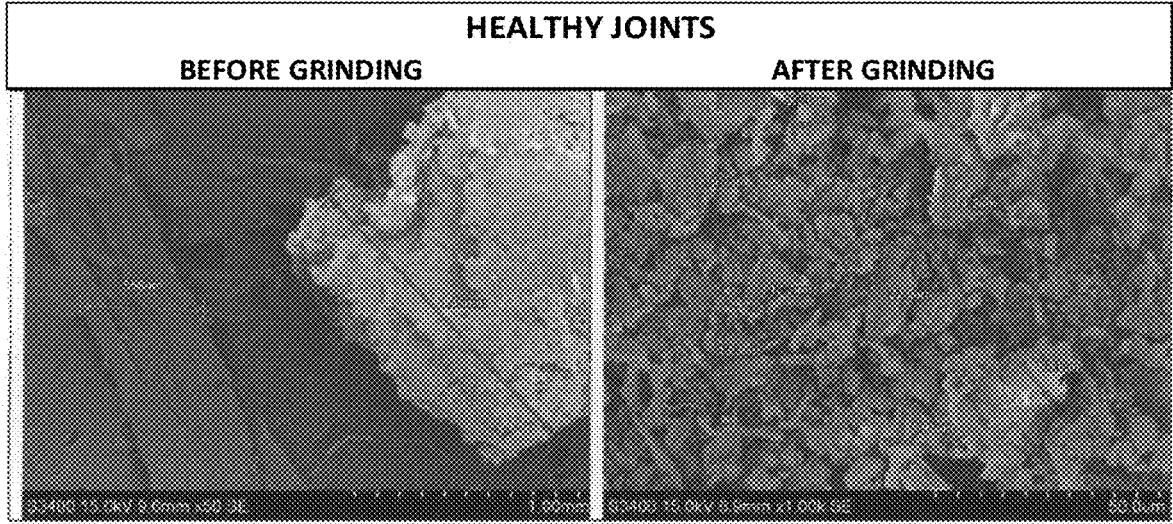
Figure 1B:
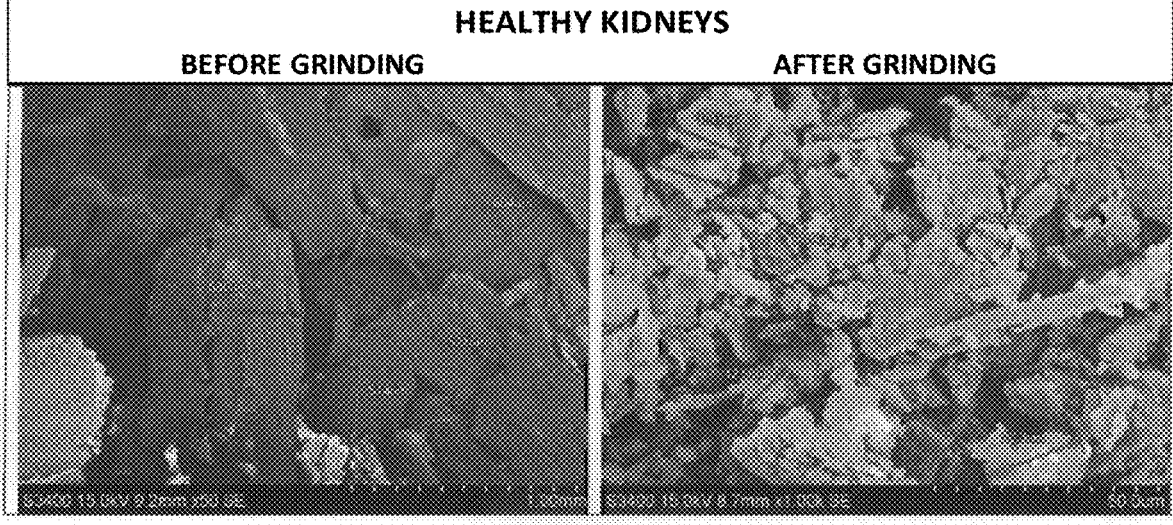
Figure 1C:
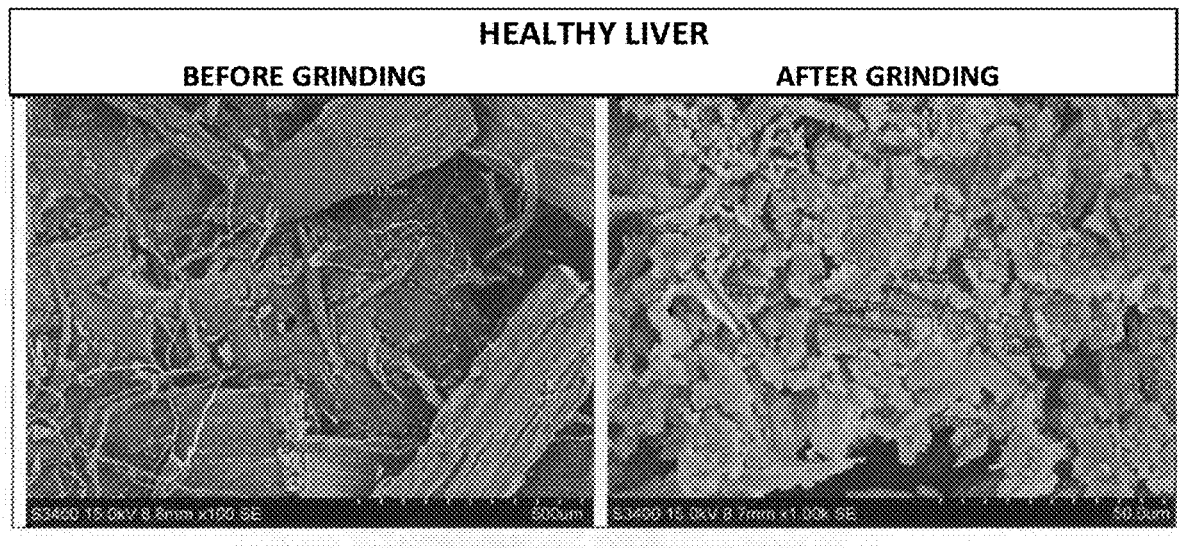
FIG. 1C shows microscope photos with determined particle sizes of "healthy liver", "healthy nerves", and "chamomile" before and after grinding.
Figure 1C:
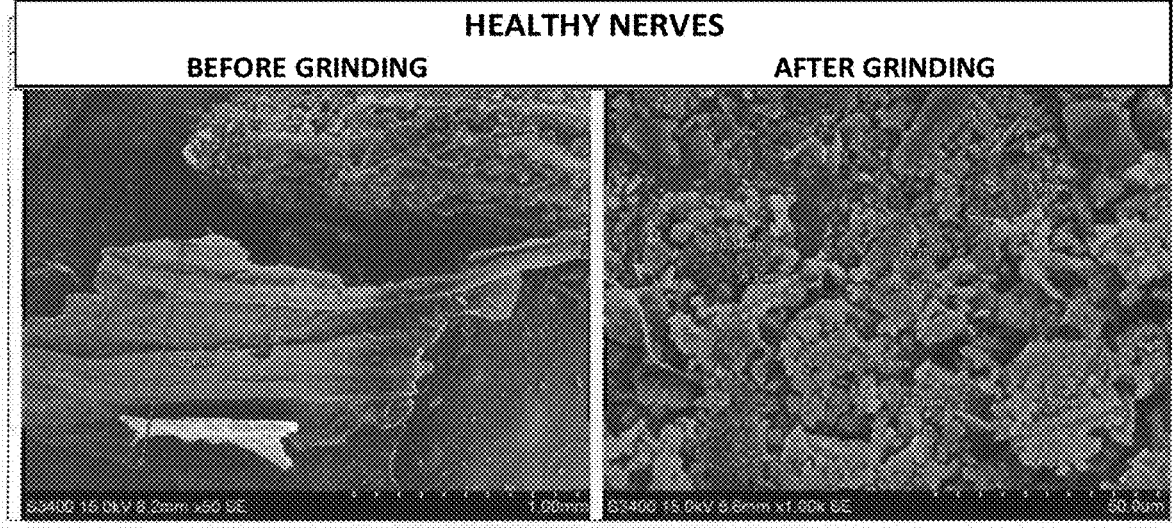
Figure 1C:
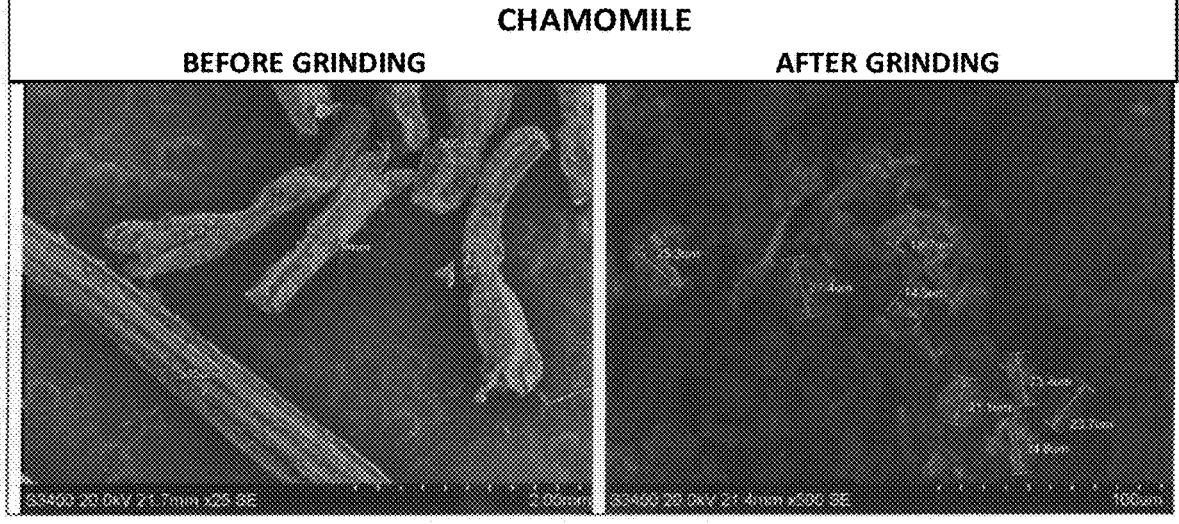

The results of microscopic examinations obtained for various herbal mixtures (labelled as: "healthy stomach", "healthy pancreas", "healthy vessels", "healthy joints", "healthy kidneys", "healthy liver", "healthy nerves", "chamomile") is shown in FIGS. 1A, 1B, and 1C.

The analysis of the surface structure of the samples before and after milling was performed with the help of the Hitachi S 3400N Scanning Electron Microscope using the high vacuum (SE) mode. The samples were sprayed with a layer of gold. Surface structure analysis was performed for various magnifications. FIGS. 1A, 1B, and 1C contain exemplary microscope photos with the determined particle sizes.

It was found that the observed particle sizes in all tested powder samples of the preparation obtained according to the invention were always smaller than 150 μm. Moreover, the size of at least 90% of all grains forming the powder did not exceed 30 μm, which indicates total destruction of the raw material.

For comparison, the particle sizes of dry plant material were also measured after preliminary drying, mechanical grinding and mixing. They also shown in FIG. 1A-1C.

Water-Soluble Extractive Substances Content

The content of water-soluble extractable substances has also been determined for selected dried herbal mixtures and the powdered plant preparations obtained from them in accordance with the invention.

Each analysis was performed on a sample of 15.0 g of dry and comminuted herbal mixture and 1.65 g of plant powder obtained from the same herbal mixture by the invention method.

Each of the test samples was placed in a 500 ml round-bottom flask and 200 ml of water was added. The flasks were closed with a stopper, weighed (to the nearest 0.01 g) and left for one hour. The flasks were then connected to a reflux condenser and heated, maintaining a gentle boil for 2 hours. After cooling, the flasks containing the contents were closed again with the same stopper, weighed and replenished with water. The contents of the flasks were carefully shaken and filtered through a dry wadding tampon into a 500 ml dry flask. Using a pipette, 25 ml of the filtrate was transferred and dried at 100° C. to 105° C. to a solid mass in carefully weighed porcelain cups 7-9 cm in diameter by evaporating in a sand bath at (105±5°) C to dryness. The cups with the residues were dried at 100° C. to 105° C. to constant weight and then cooled for 30 minutes in a desiccator with anhydrous calcium chloride and weighed immediately.

The percentage of extracts ($X_1$) calculated as an absolute dry preparation is calculated according to the formula:

$$X_1 = \frac{m \times 200 \times 100}{m_1 \times (100 - W)},$$

where: m—weight of the dry residue [g]; $m_1$—sample weight [g]; W—weight loss in the drying process, [%].

The results obtained are shown in the table below.

TABLE 1

Contents of water extractable substances in a dry herbal mixture (mixer-mixture) and the invention of a plant preparation powder (cryopowder). Measurements were taken for four different herbal mixtures (labelled as: "healthy stomach", "healthy liver", "healthy joints", "healthy pancreas").

| | "HEALTHY JOINTS" | | | |
|---|---|---|---|---|
| Residue | 0.5098 | 0.5064 | 0.069 | 0.0719 |
| % | 27.17 | 27.01 | 33.45 | 34.86 |
| Avg. % | 27.09 | | 34.155 | |
| RSD | −0.3 | | 2.06 | |
| | "HEALTHY PANCREAS" | | | |
| Residue | 0.6837 | 0.6708 | 0.0871 | 0.0895 |
| % | 36.46 | 35.78 | 42.23 | 43.39 |
| Avg. % | 36.12 | | 42.81 | |
| RSD | −0.94 | | 1.35 | |
| | "HEALTHY STOMACH" | | | |
| Residue | mixture (15 g) | | cryopowder (1.65 g) | |
| | 0.6142 | 0.6271 | 0.0915 | 0.0894 |
| % | 35.87 | 36.62 | 44.36 | 43.35 |
| Avg. % | 36.245 | | 43.855 | |
| RSD | 1.03 | | −1.15 | |
| | "HEALTHY LIVER" | | | |
| Residue | 0.5227 | 0.5095 | 0.0702 | 0.0702 |
| % | 30.72 | 29.94 | 34.04 | 34.04 |
| Avg. % | 30.33 | | 34.04 | |
| RSD | −1.27 | | 0 | |

The results obtained confirm that the content of substances extractable by water is significantly higher (each time at least 10 times higher) in the plant preparation powder obtained according to the invention than in the dry herbal mixture used to produce it. This content exceeds 30% of weight, is advantageously higher than 35% of weight, especially advantageously higher than 40% of the preparation according to the invention.

Example 3: Microgranules and the Way of Obtaining them

Characteristics of Microgranules

The microgranules were made from a powdered plant preparation according to the invention obtained in the way described in example 1. The microgranules retained all the advantages of powder from which they were produced. In particular, the high content of water-soluble extrinsic substances, the high bioavailability of natural bio-logically active substances, and the beneficial pharmacological effects on the human body.

Preparation of Microgranules

Microgranules can be produced using any known granulation technique. In the example realization, the production of microgranules by wet granulation technique includes the following stages: preparation of binding (adhesive) solution, mixing of powdered plant preparation with filler, wetting with binding (adhesive) solution, wet granulation, drying granules and calibration of granules.

Preparation of Bonding Solution (Adhesive)

An aqueous solution of carboxymethyl cellulose (CMC) with a concentration of not more than 2% by weight is used as a beneficial binding agent. The CMC solution is prepared in a reactor with a mixer-drum. Purified water and CMC are introduced into the reactor (RD—Changzhou Jiafa Granulating Drying Equipment Co., LTD) and mixed, preferably for 5-10 minutes. The mixture is allowed to swell and completely dissolve the CMC by periodically agitating the mixture. The finished solution should be clear and homogeneous.

Mixing of Powdered Plant Preparation with Filler

Starch or lactose is used as a filler. Mixing the powdered plant preparation according to the invention with the filler takes place in a mixer (HDC—Changzhou Jiafa Granulating Drying Equipment Co., LTD). The powdered plant preparation and filler is loaded into a mixer and mixed, preferably for 5-10 minutes at a mixer speed of 50 rpm. The amount of filler should not exceed 1% of the final weight of the granulate.

Moistening with a Bonding Solution (Adhesive)

Moistening of the powdered plant preparation mixture with the filler is carried out in a mixer. For this purpose, the previously prepared binding solution is added to a mixer (CM-1) with a mixture of a powdered plant preparation with a filler and mixed for 30 minutes at a mixer speed of 20 rpm. The volume of added binding solution should not exceed two volumes of the powdered plant preparation.

Wet Granulation

Wet granulation is carried out in a granulator (GR 185—Zavod Tekhogicheskogo Oborudovaniya, Mariupol, Ukraine) using a sieve with a hole size of 3 mm or 5 mm (depending on type of product). The resulting wet granules are subjected to drying.

Drying of Granules

The wet granules are fed into a fluidised bed granulator (FL-100—Changzhou Jiafa Granulating Drying Equipment Co., LTD) and air dried with a temperature of 50° C. for three hours. The residual moisture content of the granules should not exceed 5%. The dried granules are calibrated.

Calibration of Granules

The granules are calibrated in a calibration mill (GZL-180—Changzhou Jiafa Granulating Drying Equipment Co., LTD) through a 1.5 mm or 2 mm hole size screen (depending on type of product).

Example 4: Tablets and how to Obtain them

Tablet Making

The production of tablets involves the following steps: mixing granules with calcium stearate, tableting and dedusting and then packaging.

Mixing of Granules with Calcium Stearate

Calcium stearate is weighed out in the required amount according to the recipe and loaded into the mixer together with the granules. Mixing is carried out for (5-10) minutes at a mixing speed of 20 rpm.

Tabletting and Dedusting

Tabletting of granules is carried out in a tablet (RTM-41—Zavod Tekhogicheskogo Oborudovaniya, Mariupol, Ukraine). During tableting the weight and quality of tablets is controlled (durability, appearance). The tablets are dedusted and passed to packing.

Confectioning.

Tablets are packed in blisters or in plastic or glass bottles. Tablets in blister packs are placed in cartons.

Tablet Characteristics

The tablets were made from microgranules according to the invention obtained in the way described in example 3. The tablets retained all the advantages of the microgranules they were made from. In particular, the high content of soluble extractable substances in water, the high bioavailability of natural biological active substances, and the associated beneficial pharmacological effects on the human body. At the same time, the total content of additives (such as calcium stearate, potato starch, carboxymethyl cellulose) did not exceed 3% by weight of the tablet.

On the basis of the above-mentioned herbal mixtures, the following tablets were obtained, according to the invention:

"HEALTHY STOMACH"

Active substances: 1 tablet (0.85 g) contains 153 mg of marshmallow root, 136 mg of chamomile flower, 93.5 mg of yarrow aerial part, 93.5 mg of greater plantain leaf, 93.5 mg of licorice root, 93.5 mg of tormentil root, 93.5 mg of calendula flower, 68 mg of ginger root. Other ingredients: calcium stearate, potato starch, carboxymethylcellulose.

"HEALTHY LIVER".

Active substances: 1 tablet (0.85 g) contains 119 mg of sandy everlasting flower, 119 mg of corn silk, 119 mg of dandelion root, 119 mg of milk thistle fruit, 119 mg of chamomile flowers, 119 mg of bur marigold aerial parts, 110.5 mg of peppermint leaves.

Other ingredients: calcium stearate, potato starch, carboxymethylcellulose.

"HEALTHY JOINTS".

Active substances: 1 tablet (0.85 g) contains glucosamine 170 mg, willow's bark 144.5 mg, cowberry leaves 68 mg, bur marigold aerial part 51 mg, knotgrass aerial part 51 mg, pine needles 51 mg, burdock root 51 mg, bean pod 51 mg, dog rose fruit 42.5 mg, birch leaves 42.5 mg, laurel leaves 34 mg, chamomile flower 34 mg, hop strobile 34 mg;

Other ingredients: calcium stearate, potato starch, carboxymethyl cellulose.

"HEALTHY PANCREAS".

Active substances: 1 tablet (0.85 g) contains 187 mg of bilberry leaves, 136 mg of bean pod, 136 mg of nettle leaves, 119 mg of dandelion root; 119 mg of burdock root, 42.5 mg of dog rose fruit, 42.5 mg of marshmallow root, 42.5 mg of elecampane root.

Other ingredients: calcium stearate, potato starch, carboxymethyl cellulose.

"HEALTHY VESSELS".

Active substances: 1 tablet (0.85 g) contains 85 mg of cowberry leaves, 85 mg of birch leaves, 76.5 mg of dog rose fruit, 76.5 mg of common periwinkle aerial parts, 76.5 mg of buckwheat flower, 76.5 mg of pine needles, 51 mg of buckthorn bark, 51 mg of hawthorn flower and leaves, 51 mg of melilot aerial part, 51 mg of maral root, 42.5 mg of corn silk, 42.5 mg of horsetail aerial part, 42.5 mg of peppermint leaves, 42.5 mg of horse chestnut seeds.

Other ingredients: calcium stearate, potato starch, carboxymethyl cellulose.

"HEALTHY KIDNEYS".

Active substances: 1 tablet (0.85 g) contains 144.5 mg of knotgrass aerial part, 136 mg of horsetail aerial part, 102 mg of black elder flowers, 93.5 mg of bur marigold aerial part, 93.5 mg of chamomile flowers, 85 mg of cowberry leaves, 85 mg of peppermint leaves, 85 mg of dill seed.

other ingredients: calcium stearate, potato starch, carboxymethylcellulose.

"HEALTHY NERVES".

Active substances: 1 tablet (0.85 g) contains 127.5 mg of hawthorn flower and leaves, 127.7 mg of linden flower, 127.5 mg of motherwort aerial part, 127.5 mg of peppermint leaves, 119 mg of hop strobile, 102 mg valerian root, 93.5 mg of dill seed.

Other ingredients: calcium stearate, potato starch, carboxymethyl cellulose.

The invention claimed is:

1. A method of obtaining a powdered plant preparation, said method comprising:
   a) freezing a plant material to a temperature below −90° C. to obtain a frozen plant material,
   b) grinding the frozen plant material at a temperature of −150° C. to −15° C. in a vibrating mill at a frequency above 30 Hz for 1 to 15 minutes, to obtain a powdered plant material, and
   c) separating the powdered plant material to obtain a fraction with a grain size not exceeding 400 μm, wherein
   in step a) the plant material is frozen with liquid nitrogen under pressure of from 0.15 to 0.25 atm.

2. The method according to claim 1, wherein in step b), said grinding is carried out in said temperature below −70° C.

3. The method according to claim 1, wherein in step c), said separating is by sieving in a sieve with an aperture diameter of not more than 400 μm.

4. The method of claim 1, where said frequency is between 35 and 37 Hz.

5. The method of claim 1, wherein said grinding is between 5 and 10 minutes.

6. The method of claim 1, wherein said fraction is below 150 μm.

7. The method of claim 1, wherein said grinding is carried out in said temperature below −90° C.

8. A method of obtaining a powdered plant preparation, said method comprising:
   a) freezing a plant material to a temperature below −90° C. to obtain a frozen plant material, b) grinding the frozen plant material at a temperature of −150° C. to −15° C. in a vibrating mill at a frequency above 30 Hz for 1 to 15 minutes, to obtain a powdered plant material, and c) separating the powdered plant material to obtain a fraction with a grain size not exceeding 400 μm, wherein in step b) said grinding occurs in a grinding chamber cooled with liquid nitrogen at a pressure of from 0.15 to 0.25 atm.

9. The method of claim 8, wherein in step b), said grinding is carried out in said temperature below −70° C.

10. The method of claim 8, wherein in step c), said separating is by sieving in a sieve with an aperture diameter of not more than 400 μm.

11. The method of claim 8, where said frequency is between 35 and 37 Hz.

12. The method of claim 8, wherein said grinding is between 5 and 10 minutes.

13. The method of claim 8, wherein said fraction is below 150 μm.

14. The method of claim 8, wherein said grinding is carried out in said temperature below −90° C.

15. A method of obtaining a powdered plant preparation, said method comprising:

a) freezing a plant material to a temperature below −90° C. to obtain a frozen plant material, b) grinding the frozen plant material at a temperature of −150° C. to −15° C. in a vibrating mill at a frequency above 30 Hz for 1 to 15 minutes, to obtain a powdered plant material, and c) separating the powdered plant material to obtain a fraction with a grain size not exceeding 400 μm, wherein prior to said freezing, the plant material has a water content of 6% to 8%.

16. The method of claim 15, wherein in step b), said grinding is carried out in said temperature below −70° C.

17. The method of claim 15, wherein in step c), said separating is by sieving in a sieve with an aperture diameter of not more than 400 μm.

18. The method of claim 15, where said frequency is between 35 and 37 Hz.

19. The method of claim 15, wherein said grinding is between 5 and 10 minutes.

20. The method of claim 15, wherein said fraction is below 150 μm.

21. The method of claim 15, wherein said grinding is carried out in said temperature below −90° C.

* * * * *